(12) United States Patent
Kobzeff et al.

(10) Patent No.: US 6,586,213 B2
(45) Date of Patent: Jul. 1, 2003

(54) PROCESS FOR CLARIFICATION OF XANTHAN SOLUTIONS AND XANTHAN GUM PRODUCED THEREBY

(75) Inventors: Joseph M. Kobzeff, Boulder, CO (US); Daniel E. Mead, Spring Valley, CA (US); Todd A. Talashek, San Diego, CA (US); Don DiMasi, San Diego, CA (US)

(73) Assignee: CP Kelco U.S., Inc., Wilmington, DE (US)

( * ) Notice: Subject to any disclaimer, the term of this patent is extended or adjusted under 35 U.S.C. 154(b) by 0 days.

(21) Appl. No.: 09/833,559

(22) Filed: Apr. 13, 2001

(65) Prior Publication Data

US 2002/0031525 A1 Mar. 14, 2002

Related U.S. Application Data

(60) Provisional application No. 60/196,926, filed on Apr. 14, 2000.

(51) Int. Cl.[7] .......................... C12P 19/06; C08B 37/00
(52) U.S. Cl. ...................... 435/104; 435/101; 435/274; 536/114; 536/123; 536/123.1; 536/127
(58) Field of Search .............................. 435/101, 104, 435/274; 536/114, 123, 123.1, 127

(56) References Cited

U.S. PATENT DOCUMENTS

| | | | |
|---|---|---|---|
| 3,659,026 A | | 4/1972 | Schuppner, Jr. et al. .... 424/361 |
| 4,010,071 A | | 3/1977 | Colegrove ...................... 195/7 |
| 4,466,889 A | * | 8/1984 | Miller et al. ............ 252/8.55 D |
| 4,654,086 A | * | 3/1987 | Baird et al. .................. 106/206 |
| 4,874,854 A | * | 10/1989 | Colegrove et al. ........... 536/114 |
| 4,904,586 A | | 2/1990 | Ballerini et al. ............. 435/114 |
| 5,354,671 A | | 10/1994 | Pollock ...................... 435/101 |
| 5,416,206 A | | 5/1995 | Nagura et al. ............... 536/114 |
| 5,493,015 A | | 2/1996 | Murofushi et al. ......... 536/127 |
| 5,580,763 A | | 12/1996 | Honma et al. ............... 435/104 |
| 5,595,892 A | | 1/1997 | Murofushi et al. ......... 435/104 |
| 5,679,556 A | | 10/1997 | Homma et al. .............. 435/104 |
| 5,702,927 A | | 12/1997 | Murofushi et al. ......... 435/104 |
| 5,705,368 A | | 1/1998 | Murofushi et al. ......... 435/104 |
| 5,864,034 A | | 1/1999 | Murofushi et al. ......... 536/124 |
| 5,994,107 A | | 11/1999 | Murofushi et al. ......... 435/104 |

FOREIGN PATENT DOCUMENTS

| | | |
|---|---|---|
| EP | 0078621 | 5/1983 |
| EP | 0549230 | 6/1993 |
| GB | 2111520 | 7/1983 |
| JP | 8-154695 | 6/1996 |

* cited by examiner

*Primary Examiner*—Francisco Prats
(74) *Attorney, Agent, or Firm*—Banner & Witcoff, Ltd.

(57) ABSTRACT

A process is disclosed for clarifying an aqueous xanthan gum solution comprising treatment of the xanthan solution with at least one chelating agent, surfactant, organic acid, or a mixture thereof, and with a protease enzyme or a lysozyme and a protease enzyme. Also disclosed is a highly purified solid xanthan gum and compositions containing the same, wherein the gum is obtained from the clarified xanthan gum solution.

24 Claims, No Drawings

PROCESS FOR CLARIFICATION OF XANTHAN SOLUTIONS AND XANTHAN GUM PRODUCED THEREBY

This application claims the benefit of U.S. Provisional Patent Application No. 60/196,926, filed Apr. 14, 2000.

BACKGROUND OF THE INVENTION

1. Field of the Invention

The present invention relates to an improved process for the clarification of aqueous xanthan solutions and the high purity xanthan gum produced thereby.

2. Related Background Art

Xanthan gums are hydrophilic polysaccharides which are obtained by the fermentation of appropriate nutrient media with microorganisms of the genus Xanthomonas. When dissolved in water in low concentration, xanthan gums impart a viscosity to the aqueous solution. The resulting viscosified solutions are used in a wide variety of industrial applications, such as in the manufacture of ingestible products, such as food products (sauces, ice creams, etc.), and in oil field drilling fluids. Xanthan viscosified solutions are particularly useful in applications where it is desirable to suspend solid materials in the aqueous medium.

During commercial preparation of most xanthan gums, the solid xanthan is recovered by precipitation from the fermentation broth in which it is made. Generally, it is not feasible to separate all extraneous fermentation solids before this precipitation step, so that the dried solid xanthan gum recovered in this manner normally contains some water insoluble solids, such as nonviable bacterial cells and other cellular debris. These solids, of course, do not dissolve when the xanthan is re-dissolved in water. While the presence of these solids is not objectionable in many cases, it is problematic in compositions or applications where a completely clear viscosified solution is desired.

Methods evaluated for overcoming this problem have included enzyme treatments. For example, U.S. Pat. No. 4,010,071 discloses a method of clarifying xanthan solutions by treating with an alkaline protease. EP 0078621 and GB 2111520 disclose a process for clarifying xanthan gum solutions by treatment of the solution with an acid or neutral protease, followed by increasing the pH of the solution to 8 to 13. U.S. Pat. No. 5,595,892 discloses a method for recovering and purifying xanthan gum from a fermentation broth by heating the broth to a temperature of 45° C. to 80° C. at a pH of 7.0 to 12.5, and then treating the solution stepwise with an alkaline protease and a lysozyme. EP 0549230, JP 8154695 and U.S. Pat. Nos. 5,679,556, 5,702,927, 5,705,368 and 5,994,107 disclose related methods wherein a fermentation broth is heated at a temperature of 45° C. to 70° C. at a pH of at least 9.0, followed by enzyme treatment, wherein the order of alkaline protease and a lysozyme enzyme treatments is interchangeable.

Japan Patent Appln. No.8 [1996]-154695 discloses another related method wherein a fermentation broth is heated at a temperature of 45° C. to 70° C. at a pH of at least 9.0, treated with a polyphosphate and subjected to treatment with an alkaline protease and a lysozyme. Polyphosphate was the only chelating agent useful in this process.

Although these methods may provide xanthan gum solutions with some improvement in clarity, these methods require several processing steps, sometimes under different processing conditions, which may result in increased manufacturing costs or due to the high pH treatments, cause degradation (de-acetylation and/or de-polymerization) of the xanthan gum. Accordingly, it would be advantageous to provide a simplified, mild and effective process for the preparation of clarified xanthan gum solutions and high purity xanthan gum.

SUMMARY OF THE INVENTION

This invention relates to a process for the preparation of a clarified aqueous xanthan gum solution. The process comprises the steps of treating a xanthan solution with at least one treating agent selected from a chelating agent, surfactant, organic acid or a mixture thereof, and treating with a protease enzyme or a lysozyme and a protease enzyme. The treating agent may be comprised of one or more chelating agents, one or more surfactants, one or more organic acids, or any mixture thereof. The enzyme treatment process may be conducted at a temperature of about 400° C. to about 800° C. at a pH of about 6 to about 8. This invention also relates to the purified solid xanthan gum, prepared by the process of this invention, which provides substantially clear xanthan gum solutions on dissolution in water. In addition, this invention relates to compositions containing the purified xanthan gum described herein.

DETAILED DESCRIPTION OF THE INVENTION

In accordance with this invention, aqueous solutions of xanthan gum, containing suspended solids and fermentation cellular debris resulting from fermentation of Xanthomonas, may be clarified by a process comprising treating the xanthan solution with one or more chelating agents, one or more surfactants, one or more organic acids, or a mixture thereof, optionally with heating, and treating with a lysozyme and a protease enzyme. In another embodiment of this invention, aqueous solutions of xanthan gum may be clarified by a process comprising treating the xanthan solution with one or more chelating agents and treating with a protease enzyme. Advantageously, and in contrast to many prior art processes, the process of this invention does not require heating the xanthan gum solution at a pH of 9 or greater. Such high pH treatment typically results in partial or complete de-acetylation and may result in de-polymerization of the xanthan polysaccharide. Use of the near neutral pH processing conditions in the present invention provides a high purity xanthan gum product that retains substantially all of the characteristics and chemical integrity of the xanthan polysaccharide as produced by fermentation of the Xanthomonas bacteria. Advantageously, the high purity xanthan gum produced by the process of this invention possesses about 90% to 100% of the acetate concentration of the fermentation-derived xanthan gum (i.e., 10% or less of the acetate is lost during processing).

In one embodiment, the process of this invention may be conducted in a stepwise manner, wherein the xanthan solution is first treated with the chelating agent(s), surfactant(s), organic acid(s), or mixture thereof, then treated with the lysozyme and protease enzyme. In another embodiment, the process of this invention may be conducted in the stepwise manner wherein the xanthan solution is treated with chelating agent(s) then treated with a protease enzyme. Alternatively, the process may be conducted as a single operation wherein the xanthan solution is simultaneously treated with at least one chelating agent(s), surfactant(s), organic acid(s), or mixture thereof, and a protease enzyme or a lysozyme and a protease enzyme.

Advantageously, the process for producing clarified xanthan solutions described herein provides xanthan solutions that may be used, if desired after appropriate dilution, without any further chemical or mechanical treatment. The process of this invention provides for the substantially complete elimination of suspended cells from xanthan solutions. High purity xanthan gum may be isolated from these clarified solutions using conventional isolation procedures (e.g., precipitation with a non-solvent (e.g., isopropanol) followed by isolation of the precipitated product). Dissolution of this high purity xanthan gum in water provides a substantially crystal clear xanthan solution. A substantially crystal clear solution, according to this invention, has a light transmittance greater than about 90%. Light transmittance may be measured at any wavelength in the visible spectrum using conventional techniques and equipment (e.g., commercially available spectrophotometers). The light transmittance is typically measured at wavelengths of about 600 nm to 650 nm. Light transmittance may be determined for several types of xanthan gum solutions: untreated broth, partially treated broth (e.g., broth treated with only a chelating agent, an organic acid, surfactant, or a mixture thereof or broth treated only with a protease and/or lysozyme), treated broth, or reconstituted xanthan gum solutions (using xanthan gum isolated from treated broth). The substantially crystal clear solutions described herein, having a light transmittance greater than 85%, are aqueous solutions containing 1% by weight of the high purity xanthan gum, isolated from a broth treated by the method according to this invention. The light transmittance of these solutions was measured at a wavelength of 620 nm. Preferably, the aqueous solutions containing about 1% by weight of the high purity xanthan gum have a light transmittance of greater than about 90%, and more preferably, have a light transmittance of greater than about 93%.

Significantly, the high purity xanthan gum produced by the process of this invention provides low pH (pH less than 6) xanthan solutions with enhanced clarity. As compared to low pH solutions prepared with conventional xanthan gum, solutions prepared with the high purity xanthan gum of this invention have higher light transmittance. Advantageously, the high purity xanthan gum of this invention forms a 1% by weight solution having a transmittance of at least 75% at pH 5.5.

Accordingly, the high purity xanthan gum of the present invention may be used to provide improved low pH compositions having enhanced clarity. This is especially important for viscosified low pH compositions such as low pH (acidic) food products and household products where the clarity of the product enhances the value and/or consumer acceptance of the product.

The aqueous solutions of xanthan gum solutions that may be clarified using the process of this invention include the whole fermentation broth containing xanthan obtained by fermentation of a xanthan producing microorganism in a nutrient medium, solutions obtained by addition of isolated xanthan gum to aqueous media and partially purified xanthan gum solutions. The aqueous solutions of xanthan gum containing suspended undesirable fermentation solids useful in the process of this invention may contain about 0.1% to about 10% xanthan gum by weight of the total weight of the solution. Any aqueous solution containing any of the known xanthan gums, which may also be described as Xanthomonas hydrophilic colloids, may be used in the practice of this invention. It is preferred to use the aqueous solutions of the colloid produced by the bacterium *Xanthomonas campestris*, which compound and its preparation are fully described in U.S. Pat. No. 3,659,026.

Other Xanthomonas colloidal materials (xanthan gums) may be prepared by repeating the procedure describe in this patent for producing the *Xanthomonas campestris* colloid by using as the producing microorganism other known Xanthomonas bacteria i.e., *Xanthomonas carotate, Xanthomonas incanae, Xanthomonas begoniae, Xanthomonas malverum, Xanthomonas vesicatoria, Xanthomonas papavericola, Xanthomonas translucens, Xanthomonas vasculorum* and *Xanthomonas hederae* in place of the *Xanthomonas campestris*.

The first step of the process of this invention comprises treating an aqueous xanthan solution with a treating agent selected from at least one chelating agent, surfactant, organic acid, or a mixture thereof, optionally with heating. Preferably, the process is conducted whereby the pH of the xanthan solution containing at least one chelating agent, surfactant, organic acid, or a mixture thereof, is adjusted to a pH of about 6 to about 8 prior to the treatment with a protease enzyme or lysozyme and protease enzyme, as described herein.

Treatment with the treating agents may be accomplished by mixing the chelating agent(s), surfactant(s), organic acid(s), or mixture thereof, in any form (e.g., neat or in solution) or in any order into the aqueous xanthan solution. Treatment with these treating agents may be conducted in a stepwise manner or may be conducted as a single operation comprising simultaneous treatment with the treating agents. In this invention, each embodiment of the process, and each process step thereof, may be conducted in a stepwise manner or, alternatively, as a single operation comprising a simultaneous treatment. As used herein, "simultaneous" means that the recited reagents (e.g., the treating agent (the chelating agent(s), surfactant(s), and/or organic acid(s)) and the protease enzyme or lysozyme and protease enzyme) used in such a simultaneous treatment step are present in the xanthan solution during the treatment. Such simultaneous treatment does not require that the reagents be added as a mixture or at one time. The reagents may be added in any order over any period of time, provided that the recited reagents are present in the xanthan solution during the treatment.

The treating agent used herein may be comprised of a single agent or a combination of agents, according to the different embodiments described herein. For example, a chelating agent may be used individually, or in combination with another chelating agent or may be used in combination with one or more surfactants and/or one or more organic acids. A surfactant may be used individually or in combination with another surfactant, one or more chelating agents and/or one or more organic acids. An organic acid may be used individually or in combination with another organic acid, one or more chelating agents and/or one or more surfactants. These agents may be used individually or combined in any manner, together with a protease enzyme or a lysozyme and a protease enzyme, to provide the high purity xanthan gum of this invention. Preferred treating agent combinations include the use of two chelating agents, the use of at least one chelating agent in combination with at least one surfactant, the use of one or more organic acids in combination with at least one surfactant; or the use of two surfactants.

Chelating agents that are suitable for use in the process of this invention are compounds or compositions that are capable of sequestering multivalent metal ions (e.g., $Mg^{+2}$, $Ca^{+2}$, etc.) in the aqueous xanthan solution by forming poly-dentate complexes with the metal ions, forming a precipitate with the metal ions or adsorbing the metal ions. Preferably, the chelating agents are water or water-alcohol soluble compounds or compositions and are alkali metal or alkaline earth salts of organic and/or inorganic acids or organic/inorganic acid salts of basic (amine-containing)

organic compounds, as well as the organic and/or inorganic acids or the basic compounds themselves. Other chelating agents useful in the process of this invention are cationic ion exchange resins and carbonic acid and carbonic acid salts. Salt compounds and compositions that are particularly useful in the process of this invention include the salts of ethylenediamine tetraacetic acid, phosphoric acid, metaphosphoric acid, carbonic acid, citric acid, tartaric acid, gluconic acid, glutamic acid, pyrophosphoric acid, polyphosphoric acid, metaphosphoric acids, saccharic acid, ethyleneglycol-bis-(beta-aminoethyl ether)-N,N,N',N'-tetraacetic acid (EGTA), ethylenediamine, 2,3-diaminobutane, 1,2-diaminocyclohexane, triaminotriethylamine and the like. Useful salts may include the mono-, di-, tri-and/or tetra-metal salts of the above acids and the mono-, di-or tri-acid salts of the above bases, as appropriate. Preferably, the chelating agents used in the process of this invention include salts of ethylenediamine tetraacetic acid, citric acid, phosphoric acid, pyrophosphoric acid, polyphosphoric acid, carbonic acid, metaphosphoric acid, and ethylenediamine. Examples of useful chelating agents include, but are not limited to, disodium ethylenediamine tetraacetate, dipotassium ethylenediamine tetraacetate, tetrasodium ethylenediamine tetraacetate, tetrapotassium ethylenediamine tetraacetate, trisodium citrate, tripotassium citrate, sodium hexametaphosphate, potassium hexametaphosphate, sodium polyphosphate, potassium polyphosphate, sodium pyrophosphate, potassium pyrophosphate, monosodium phosphate, monopotassium phosphate, disodium phosphate, dipotassium phosphate, trisodium phosphate, tripotassium phosphate, sodium bicarbonate, sodium carbonate, potassium carbonate, potassium bicarbonate, a cationic ion exchange resin, ethylenediamine dihydrochloride, ethylenediamine diacetate, ethylenediamine lithium salt, ethylenediamine dihydroiodide and the like.

Surfactants that are suitable for use in the process of this invention are compounds or compositions that are capable of forming aqueous emulsions in the presence of hydrophilic and hydrophobic substances (solids or liquids). Preferably, the surfactants are water or water-alcohol soluble compounds or compositions. Examples of useful surfactants include, but are not limited to, lecithin, monoglycerides, tartaric esters of monoglycerides, phosphated monoglycerides (e.g., as the monosodium salt), lactylated monoglycerides, acetylated monoglycerides, succinylated monoglycerides, ethoxylated monoglycerides, sorbitan esters, polysorbates, polyglycerol esters, sucrose esters, sodium stearoyl lactylate, propylene glycol esters and the like.

Organic acids that are suitable for use in the process of this invention are water or water-alcohol soluble compounds or compositions. Examples of useful organic acids include α-hydroxy acids, linear carboxylic acids or bactericidal or preservative acids, such as lactic acid, benzoic acid, propionic acid, sorbic acid, acetic acid and the like. Preferably, lactic acid is used in the process of this invention.

Optionally, the process may be conducted by heating the xanthan solution prior to after addition of the at least one chelating agent, surfactant, organic acid, or a mixture thereof, to a temperature of about 50° C. to about 120° C. Preferably, the solution may be heated for about 1 to about 30 minutes at about 50° C. to about 120° C. This treatment time period refers to the length of time that the solution is heated at a desired temperature between about 50° C. to about 120° C. This time period does not include the time required to heat the xanthan solution to that desired temperature. Of course, the length of time that it takes to heat the xanthan solution to the desired temperature will vary significantly depending on the size and volume of xanthan solution to be treated. For example, whereas it may take only several minutes to increase the temperature of a small volume (e.g., 50 milliliters or as present in in-line processing) of xanthan solution from room temperature to about 100° C., it may take several hours to similarly increase the temperature of 40,000 liters of solution (e.g., as present in batch processing). As indicated above, the xanthan solution may be heated prior to or after the addition of the chelating agent(s), surfactant(s), organic acid(s) or mixture thereof. Preferably, the pH of the xanthan solution is adjusted to a pH of about 6 to about 8 prior to heating to prevent de-acetylation or degradation of the xanthan gum during heating. Preferably, the process may be conducted by heating a xanthan solution containing the chelating agent(s), surfactant(s), organic acid(s) or mixture thereof at a temperature of about 60° C. to about 100° C. at a pH of about 6 to about 8. The heated xanthan solution may be maintained at a desired temperature of about 60° C. to about 100° C. for about 1 to about 30 minutes prior to enzyme treatment. More preferably, the xanthan solution containing the chelating agent(s), surfactant(s), organic acid(s) or mixture thereof may be maintained at a temperature of about 65° C. to about 90° C. at a pH of about 6 to about 8 for about 1 to about 30 minutes prior to enzyme treatment.

The process of this invention also comprises the step of treating the aqueous xanthan gum solution with a protease enzyme or a protease enzyme and a lysozyme. Under the reaction conditions described herein, the enzymes degrade the solid cellular debris to soluble compounds, thus clarifying the aqueous xanthan gum solution. The protease enzymes suitable for use in this process may be acid, neutral or alkaline proteases from bacterial, fungal or plant sources. Exemplary acid protease enzymes useful in the process of this invention include, but are not limited to proteases produced by microorganisms of the genus Aspergillus, such as *A. niger*, or that are present in pineapples. The neutral protease enzymes useful in the process of this invention include, but are not limited to proteases such as *Bacillus amyloliquifaciens*. The alkaline protease enzymes useful in the process of this invention include, but are not limited to, proteases produced by microorganisms of the genus Bacillus such as *B. subtilis, B. licheniformis*, and *B. pumilis*, proteases elaborated by species of Streptomyces such as *S. fradiae, S. griseus* and *S. rectus*, and proteases obtained from subtilisins, such as subtilisin Novo, subtilisin Carlsberg, including proteases such as subtilopeptidase A and subtilopeptidase B. The lysozymes suitable for use in this process include Multifect® lysozyme obtained from Genencor, Rochester, N.Y. and lysozymes that may be obtained from any plant, animal or microbially-derived sources. The source of any of the protease enzymes or lysozymes used in the process of this invention is not critical. These enzymes and the methods of obtaining them are well known in the art. In this invention, the enzyme treatment (treatment with the lysozyme and protease enzyme) is conducted as a single operation comprising treatment with a protease enzyme or simultaneous treatment with both a protease enzyme and a lysozyme. As described above, such simultaneous treatment permits the addition of the protease enzyme and lysozyme to the xanthan solution to be conducted in any order, over any period of time, provided that both enzymes are present in the xanthan solution during the treatment. The process may be conducted such that the lysozyme is added to the xanthan solution prior to the addition of the protease enzyme. Alternatively, the protease enzyme may be added to the xanthan solution prior to the lysozyme, or the enzymes may be added at the same time. The enzyme treatment process of this invention is conducted under conditions such that the protease enzyme or both the lysozyme and protease enzyme are active and provide the desired enzymatic function. The enzyme treatment process may be conducted at a temperature of about 40° C. to about 80° C. at a pH of about 6 to about 8. Generally, the enzyme treatment process may be conducted for about 0.25 hours to about 4 hours, but is dependent on enzyme concentration and enzyme activity; lower enzyme concentration and/or activity levels may require longer treatment times. Preferably, the enzyme treatment process is conducted at a temperature of about 50° C. to about 70° C. for about 0.25 to about 3 hours at a pH of about 6.5 to about 7.5. More preferably, the enzyme treatment process is conducted at a temperature of about 50° C. to about 60° C. for about 0.5 to about 2 hours at a pH of about 6.5 to about 7.5. The temperature and pH at which different enzymes demonstrate optimal activity may vary. However, the process of the present invention is conducted at relatively mild temperatures and at nearly neutral conditions such that both the lysozyme and protease enzymes (acid, neutral or alkaline proteases) will demonstrate acceptable levels of activity to clarify the xanthan solutions.

Agitation of the aqueous xanthan mixture is not essential, although where feasible the solution is stirred or agitated mildly or periodically to avoid undue settling of the solids and promote contact with the enzymes. When a whole fermentation broth is used or when solid xanthan gum containing extraneous water-insoluble fermentation solids is used as starting materials, a specific pH adjustment is usually unnecessary but if desired, it may be accomplished by addition of an acid or a base, as appropriate. The presence of other chemical compounds, such as for example, chlorine or salts (in high concentration), which interfere with the enzymic activity of the protease enzyme or lysozyme or degrade the enzymes should, of course, be avoided.

Only minor amounts of the enzymes are necessary to effect the desired clarification. As will be readily recognized by those skilled in the art, these enzymes are commercially available in a variety of forms possessing varying levels of enzymatic activity. Accordingly, the concentration of the enzyme used may vary between the differing forms of the enzymes, between batches and between sources. It is considered within the ordinary skill of one in the art to determine the lysozyme and/or protease enzyme concentration required to obtain clarified xanthan gums solutions which can provide the high purity xanthan gum described herein.

Generally, however, the aqueous xanthan gum solution is treated with about 10 ppm to about 1000 ppm (parts per million of aqueous xanthan solution) lysozyme and/or about 0.3 ppm to 2000 ppm protease enzyme. Preferably, the aqueous xanthan gum solution is treated with about 10 ppm to about 100 ppm lysozyme and/or about 0.3 ppm to about 500 ppm protease enzyme.

It should be noted that the degree of clarification effected by treatment of the xanthan solution with the chelating agent(s), surfactant(s), organic acid(s) or mixture thereof may affect the enzyme concentrations or the time required to complete the subsequent enzyme treatment. For example, increasing the amount of the chelating agent(s), surfactant (s), organic acid(s), or mixture thereof used in this process may decrease the amount of enzymes used and/or the time required to effect clarification of a xanthan solution. It is considered within the ordinary skill of one in the art to adjust and balance the concentration and length of treatment time of the chelating agent(s), surfactant(s), organic acid(s) or mixture thereof and/or the use of heat with the concentration and length of treatment time of the lysozyme and/or protease to obtain clarified xanthan gums solutions which can provide the high purity xanthan gum described herein.

After conducting the clarification of the xanthan gum solution according to the process described herein, the purified xanthan gum may be isolated or obtained in solid form using any conventional procedure. For example, a non-solvent, such as isopropanol or an isopropanol/water mixture, may be added to the aqueous xanthan solution to precipitate the xanthan gum. This precipitated gum may be separated from the aqueous/isopropanol solution using conventional procedures, e.g., by filtration, de-watering, expression, centrifugation and the like, followed by drying. The high purity xanthan gum obtained by the process of this invention and isolated using conventional procedures, on dissolution in water, will provide substantially clear viscosified compositions having a transmittance of at least 85%, preferably, a transmittance of at least 90%, and most preferably, a transmittance of at least 93% (for solutions containing 1% by weight of the high purity xanthan gum).

Accordingly, the process of this invention for the preparation of a clarified xanthan gum solution comprises the steps of:

1) treating an aqueous solution containing xanthan gum with at least one chelating agent, surfactant, organic acid, or a mixture thereof; and 2) treating the solution with a lysozyme and a protease enzyme at a temperature of about 40° C. to about 80° C. at a pH of about 6 to about 8;

wherein said xanthan gum solution is not subjected to heating at a pH of 9 or greater.

In another embodiment, the process of this invention comprises the steps of:

1) treating an aqueous solution containing xanthan gum with at least one chelating agent; and 2) treating the solution with a protease enzyme at a temperature of about 40° C. to about 80° C. at a pH of about 6 to about 8.

Alternatively, the clarification process may be conducted as a single operation wherein step 1 and step 2 of the above processes are conducted simultaneously such that the xanthan solution is simultaneously treated with at least one chelating agent, surfactant, organic acid, or a mixture thereof, and a protease enzyme or a lysozyme and a protease enzyme. In these embodiments, the process for the preparation of a clarified xanthan gum solution comprises treating a xanthan gum with at least one chelating agent, surfactant, organic acid, or a mixture thereof, and a protease enzyme or a lysozyme and a protease enzyme at a pH of about 6 to about 8 at a temperature of about 40° C. to about 80° C.

The process for obtaining a high purity xanthan gum from a xanthan gum-containing aqueous solution comprises treating an aqueous solution containing xanthan gum according to any of the above processes and recovering the xanthan gum from the solution.

Another embodiment of this invention relates to compositions having improved clarity or performance over conventional xanthan compositions. The high purity xanthan gum solid provided by the process of this invention may be useful in any and all of the applications where conventional xanthan gums are acceptable, for example, in viscosified or gelled compositions and in compositions used for suspending solid materials. Advantageously, the high purity xanthan gum solid provided by the process of this invention may also be useful in many industrial applications where conventional xanthan gums are not acceptable. For example, the presence of solids, such as nonviable bacterial cells and other cellular debris, presents difficulties when xanthan gum is used to prepare enhanced oil recovery fluids used in oil well flooding operations. Examples of such oil recovery fluids include payzone drilling fluids, workover fluids, completion fluids, and the like. The insoluble solids can plug the small pores in the rock formations where secondary and tertiary oil recovery operations are carried out, thus leading to formation damage.

The high purity xanthan gum solid provided by the process of this invention may be useful in food products, such as clear salad dressings, beverages, and dessert gels, in household products, such as cleaners, or in personal care products, such as clear lotions, gel toothpaste, liquid soaps, styling gels, shampoos and the like. The high purity xanthan gum solid provided by the process of this invention may be especially useful in low pH (acidic) food products, such as vinegar-containing dressings, beverages and dessert gels, such as carbonated beverages or gels and fruit beverages or gels, which generally have a pH of about 3–6, in household products, such as acid-containing cleaners, and the like. Moreover, such high purity xanthan gum may be especially useful in the preparation of pharmaceutical products, such as suspensions.

It is anticipated that the method of clarification of xanthan solutions disclosed herein, will also be suitable for the clarification of solutions of other fermentation-derived polysaccharides, for example, welan gum, rhamsan gum, gellan gum, and the like.

The Examples which follow are intended as an illustration of certain preferred embodiments of the invention, and no limitation of the invention is implied. Light transmittance, determined as a percentage at 620 nm, was measured on the broth "as is" or on a reconstituted 1 wt. % xanthan gum solution in de-ionized water using a Spectronic 21 spectrometer.

EXAMPLE 1

Disodium ethylenediamine tetraacetate (2.0 grams, $Na_2EDTA$) was added to two liters of a fermentation broth, containing xanthan gum produced by *Xanthomonas campestris*, heated to a temperature of 55° C. using a hot water bath. The pH of the broth was 6.5–7.0. This mixture was mixed for 30 minutes at 55° C., followed by addition of a protease enzyme (0.44 grams, Protex 6L, Genencor International) and lysozyme (0.044 grams, Multifect® lysozyme, Genencor International). The resulting mixture was maintained at a temperature of 55° C. and mixed for two hours, then centrifuged for 5 minutes at 2000 rpm. Light transmittance at 620 nm of the resulting treated fermentation broth was 75%, whereas light transmittance of the untreated broth at 620 nm was 4%.

EXAMPLE 2

Trisodium citrate dihydrate (3.0 grams) was added to two liters of a fermentation broth, containing xanthan gum produced by *Xanthomonas campestris*, heated to a temperature of 55° C. using a hot water bath. The pH of the broth was 6.5–7.0. This mixture was mixed for 30 minutes at 55° C., followed by addition of a protease enzyme (0.44 grams, Protex 6L, Genencor International) and lysozyme (0.044 grams, Multifect® lysozyme). The resulting mixture was maintained at a temperature of 55° C. and mixed for two hours, then centrifuged for 5 minutes at 2000 rpm. Light transmittance (at 620 nm) of the resulting treated fermentation broth was 60%, whereas light transmittance (620 nm) of the untreated broth was 4%.

EXAMPLE 3

Two liters of xanthan fermentation broth were heated to 55° C. One or more organic acids (4.5 grams of an 88% lactic acid solution) was added followed immediately by neutralization with KOH to pH 7.0. Then 0.044 grams Multifect® Lysozyme and 0.44 grams Protex 6L were added. The mixture was held with mixing at 55° C. for two hours. The broth transmittance was measured to be 46%.

COMPARATIVE EXAMPLE 1

Two liters of a fermentation broth were adjusted to a pH of 10.97 with KOH and then heated to 55° C. and held with mixing for 90 minutes. The pH was then reduced to 7.38 with $H_2SO_4$. Enzymes were added (0.044 grams Multifect® 0.44 grams Protex 6L and held with mixing. The broth transmittance was measured after 2 and 6 hours. Samples were recovered after 2 and 4 hours by precipitation with isopropyl alcohol followed by drying and milling. The "2 hour" sample results are shown below as "Sample 1" and the "6 hour" sample results are shown as "Sample 2". An additional sample (2 L) of the same fermentation broth (pH 7.2) was treated with 3.0 grams of trisodium citrate dihydrate, heated to 55° C., and treated with enzymes (0.044 grams Multifect® Lysozyme, 0.44 grams Protex 6L, both from Genencor International) for 2 hours. The treated broth was recovered by precipitation in isopropyl alcohol followed by drying and milling. The results for this sample are shown as "Sample 3".

Untreated broth was also precipitated, dried, and milled as above for comparison.

The quality of the product from each treatment is shown below:

| Sample | % T[a] Broth | Visc.[b] (cP) | % T[c] | % OAc[d] | % OPy[e] |
| --- | --- | --- | --- | --- | --- |
| Untreated Broth | — | 610 | 35 | 4.08% | 4.67% |
| Sample 1 | 48% | 430 | 97 | 0.75% | 4.61% |
| Sample 2 | 48% | 440 | 97 | 0.78% | 5.21% |
| Sample 3 | 51% | 750 | 96 | 4.28% | 4.97% |

[a]% Transmittance of untreated broth
[b]Viscosity of an aqueous solution containing 1 wt % of the recovered xanthan gum
[c]% Transmittance of an aqueous solution containing 1 wt % of the recovered xanthan gum
[d]The amount (wt %) of acetate present in the recovered xanthan gum.
[e]The amount (wt %) of pyruvate present in the recovered xanthan gum.

COMPARATIVE EXAMPLE 2

Two liters of xanthan fermentation broth were treated as in Example 2. An additional two liters of the same fermentation broth were treated only with enzymes (no sodium citrate) as follows: The pH was adjusted to 7.0–7.5, and the broth was heated to about 55° C. Then 0.044 grams Multifect® Lysozyme and 0.44 grams Protex 6L (both from Genencor International) were added. The mixture was held with mixing at about 55° C. for two hours. The broth transmittance of each sample was measured and is shown below:

| Sample | Broth Transmittance |
| --- | --- |
| with sodium citrate | 44% |
| without sodium citrate | 25% |

COMPARATIVE EXAMPLE 3

A protease enzyme (0.44 grams, Protex 6L) and lysozyme (0.044 grams Multifect® Lysozyme) were added to two liters of a fermentation broth having a pH of 6.5–7.0 and containing xanthan gum produced by *Xanthomonas campestris*, heated to a temperature of 55° C. The resulting composition was mixed for two hours at a temperature of 55° C., then centrifuged for 5 minutes at 2000 rpm. Light transmittance (at 620 nm) of the resulting treated fermentation broth was 14%, whereas light transmittance (620 nm) of the untreated broth was 4%.

COMPARATIVE EXAMPLE 4

A test sample, prepared by the process of this invention, was obtained by treating two liters of xanthan gum fermentation broth with 2.2 grams of each of $KH_2PO_4$ and $K_2HPO_4$. The pH was measured to be 7.1. The xanthan solution was heated to a temperature of about 55° C., to which was added 0.044 grams of Multifect® Lysozyme and 0.44 grams of Protex 6L. The resulting solution was mixed for two hours, after which the xanthan gum was recovered by precipitation using isopropyl alcohol. The resulting xanthan gum was dried and milled. The transmittance of a 1% by weight solution of this xanthan gum was 88.8%.

A comparative sample was obtained by heating two liters of xanthan broth (pH 7.1) at a temperature of about 55° C. and adding the enzymes as above. After two hours of mixing, the product was recovered in the same manner as above and had a transmittance of 88.2%.

The pH of these two test solutions was then lowered to pH 5.5, and the transmittance was measured again. The transmittance (clarity) of the test sample (treated with phosphate) was 79.8% and the transmittance of the comparative sample was 70.6%.

Other variations or modifications, which will be obvious to those skilled in the art, are within the scope and teachings of this invention. This invention is not to be limited except as set forth in the following claims.

We claim:

1. A process for the preparation of a clarified xanthan gum solution, said process comprising the steps of:
   1) treating an aqueous solution containing xanthan gum with at least one chelating agent, surfactant, organic acid, or a mixture thereof;
   2) adding a lysozyme enzyme and a protease enzyme to the aqueous solution subsequent to or simultaneous with treating with the at least one of the chelating agent, surfactant, organic acid, or mixture thereof; and
   3) treating the aqueous solution containing xanthan gum with the lysozyme and protease enzymes at a temperature of about 40° C. to about 80° C. at a pH of about 6 to about 8;
   wherein said xanthan gum solution is not subjected to heating at a pH of 9 or greater, thereby forming a clarified xanthan gum solution in which the xanthan gum has an acetate concentration of at least about 90 percent of that of the xanthan gum in the solution before treatment.

2. A process for the preparation of a clarified xanthan gum solution, said process comprising the steps of:
   1) treating an aqueous solution containing xanthan gum with at least one chelating agent, surfactant, organic acid, or a mixture thereof;
   2) adding a protease enzyme to the aqueous solution subsequent to or simultaneous with treating with the at least one of the chelating agent, surfactant, organic acid, or mixture thereof; and
   3) treating the aqueous solution containing xanthan gum with the protease enzyme at a temperature of about 40° C. to about 80° C. at a pH of about 6 to about 8, thereby forming a clarified xanthan gum solution in which the xanthan gum has an acetate concentration of at least about 90 percent of that of the xanthan gum in the solution before treatment.

3. The process for the preparation of a clarified xanthan gum solution according to claim 1, wherein step 1 and step 2 are conducted simultaneously at a pH of about 6 to about 8 at a temperature of about 40° C. to about 80° C.

4. The process for the preparation of a clarified xanthan gum solution according to claim 2, wherein step 1 and step 2 are conducted simultaneously at a pH of about 6 to about 8 at a temperature of about 40° C. to about 80° C.

5. The process according to claims 1 or 3, wherein the aqueous xanthan solution is treated with at least one chelating agent.

6. The process according to claims 1 or 3, wherein the aqueous xanthan solution is treated with one or more surfactants.

7. The process according to claims 1 or 3, wherein the aqueous xanthan solution is treated with one or more organic acids.

8. The process according to claims 1 or 3, wherein the aqueous xanthan solution is treated with a chelating agent and one or more surfactants.

9. The process according to claim 8, wherein the aqueous xanthan solution is treated with one or more organic acids and one or more surfactants.

10. The process according to any one of claims 1 or 2, further comprising heating the xanthan solution of step 1 at a temperature of about 50° C. to about 120° C.

11. The process according to any one of claims 1 or 2, wherein the enzyme treatment is conducted at a pH of about 6.5 to about 7.5.

12. The process according to any one of claims 1 or 2, wherein the enzyme treatment is conducted at a temperature of about 50° C. to about 70° C.

13. The process according to claims 3 or 4, wherein the xanthan solution is treated at a pH of about 6.5 to about 7.5 and at a temperature of about 50° C. to about 70° C.

14. The process according to any one of claims 1 to 4, wherein the at least one chelating agent is selected from ethylenediamine tetraacetic acid, phosphoric acid, metaphosphoric acid, carbonic acid, citric acid, tartaric acid, gluconic acid, glutamic acid, pyrophosphoric acid, polyphosphoric acid, metaphosphoric acids, saccharic acid, cationic ion exchange resin, ethylenediamine and ethyleneglycol-bis-(beta-aminoethyl ether)-N,N,N',N'-tetraacetic acid or a salt thereof.

15. The process according to any one of claims 1 to 4, wherein the at least one chelating agent is selected from disodium ethylenediamine tetraacetate, dipotassium ethylenediamine tetraacetate, tetrasodium ethylenediamine tetraacetate, tetrapotassium ethylenediamine tetraacetate, trisodium citrate, tripotassium citrate, sodium hexametaphosphate, potassium hexametaphosphate, sodium polyphosphate, potassium polyphosphate, sodium pyrophosphate, potassium pyrophosphate, monosodium phosphate, monopotassium phosphate, disodium phosphate, dipotassium phosphate, trisodium phosphate, tripotassium phosphate, sodium bicarbonate, sodium carbonate, potassium carbonate, potassium bicarbonate, a cationic ion exchange resin, ethylenediamine dihydrochloride, ethylenediamine diacetate, ethylenediamine lithium salt, ethylenediamine dihydroiodide and mixtures thereof.

16. The process according to claims 1 or 3, wherein the at least one surfactant is selected from lecithin, a monoglyceride, a tartaric acid ester of a monoglyceride, a phosphated monoglyceride, a lactylated monoglyceride, an acetylated monoglyceride, a succinylated monoglyceride, an ethoxylated monoglyceride, a sorbitan ester, a polysorbate, a polyglycerol ester, a sucrose ester, a sodium stearoyl lactylate and a propylene glycol ester.

17. The process according to claims 1 or 3, wherein the at least one organic acid is selected from lactic acid, benzoic acid, propionic acid, sorbic acid, acetic acid.

18. A process for preparing a high purity xanthan gum, the process comprising:

preparing a clarified xanthan gum solution according to the process of any one of claims 1 to 4; and isolating the xanthan gum from the clarified xanthan gum solution.

19. The process according to claim 18, wherein an aqueous solution of said xanthan gum possesses a transmittance of at least 90%.

20. A process for preparing an enhanced oil recovery fluid comprising preparing a xanthan gum according to the process of claim 18.

21. A process for preparing an ingestible product comprising preparing a xanthan gum according to the process of claim 18.

22. The process according to claim 21, wherein said product is a food product or a pharmaceutical composition.

23. A process for preparing a cleaner or personal care product comprising preparing a xanthan gum according to the process of claim 18.

24. The process according to claim 23, wherein said product is a gel toothpaste, a liquid soap, a styling gel, or a shampoo.

* * * * *

UNITED STATES PATENT AND TRADEMARK OFFICE
CERTIFICATE OF CORRECTION

PATENT NO.     : 6,586,213 B2
DATED          : July 1, 2003
INVENTOR(S)    : Joseph M. Kobzeff, et al.

It is certified that error appears in the above-identified patent and that said Letters Patent is hereby corrected as shown below:

Column 2,
Lines 17 and 18, replace as follows: -- process may be conducted at a temperature of about 40°C. to about 80°C. at a pH of about 6 to about 8. This invention --

Signed and Sealed this

Twenty-fifth Day of November, 2003

JAMES E. ROGAN
*Director of the United States Patent and Trademark Office*